United States Patent
Yokota et al.

(10) Patent No.: US 6,281,323 B1
(45) Date of Patent: Aug. 28, 2001

(54) TERMINAL-MODIFIED IMIDE OLIGOMERS AND CURED PRODUCTS THEREOF

(75) Inventors: Rikio Yokota, Iruma; Masatoshi Hasegawa, Chiba; Hiroaki Yamaguchi, Ichihara, all of (JP)

(73) Assignee: Ube Industries, Ltd. (JP)

( * ) Notice: Subject to any disclaimer, the term of this patent is extended or adjusted under 35 U.S.C. 154(b) by 0 days.

(21) Appl. No.: 09/443,885

(22) Filed: Nov. 19, 1999

(30) Foreign Application Priority Data

Nov. 25, 1998 (JP) .................................................. 10-334100
Jul. 29, 1999 (JP) .................................................. 11-215343

(51) Int. Cl.[7] ............................ C08G 73/10; C08G 69/26
(52) U.S. Cl. ........................... 528/170; 528/125; 528/126; 528/128; 528/172; 528/173; 528/176; 528/179; 528/183; 528/185; 528/188; 528/220; 528/229; 528/350; 528/353; 428/411.1; 428/473.5
(58) Field of Search ..................................... 528/170, 172, 528/173, 126, 125, 128, 176, 179, 183, 185, 188, 220, 229, 350, 353; 428/411.1, 473.5

(56) References Cited

U.S. PATENT DOCUMENTS

| | | | |
|---|---|---|---|
| 4,963,645 | 10/1990 | Inoue et al. | 528/342 |
| 5,066,771 | 11/1991 | Hino et al. | 528/353 |
| 5,493,002 | 2/1996 | McGrath et al. | 528/310 |
| 5,567,800 | 10/1996 | Hergenrother et al. | 528/353 |
| 5,606,014 | * 2/1997 | Connell et al. | 528/353 |
| 5,644,022 | 7/1997 | Jensen | 528/353 |
| 5,760,168 | * 6/1998 | Hergenrother et al. | 528/353 |
| 5,817,744 | * 10/1998 | Sheppard et al. | 528/353 |

FOREIGN PATENT DOCUMENTS

| | | |
|---|---|---|
| 0 472 402 | 2/1992 | (EP) . |
| 9-71651 | 3/1997 | (JP) . |
| WO 98 40422 | 9/1998 | (WO) . |

OTHER PUBLICATIONS

Fang, X., et al: "A Study of the Thermal Cure of a Phenylethynyl–Terminated Imide Model Compound and a Phenlyethynyl–Terminated Imide Oligomer (PETI–5)"; Journal of Polymer Science, Part A (Polymer Chemistry), vol. 36, No. 3, Mar. 1997 pp. 461–470.

B. Dao, et al.: "The utility of 2–naphthol as Diels–Alder based co–reactants for bismaleimedes." High Performance Polymers, vol. 9, 1997, pp. 413–427. No month.

J.A. Johnston, et al.: "Synthesis and charcaterization of imide oligomers end–capped with 4–(phenyletynyl) phthalic anhydrides." Polymer, vol. 35, No. 22, Oct. 1994, pp. 4865–4873.

T. Takekoshi, et al.: "High–temperature thermoset polyimides containing disubstituted acetylene end groups." Polymer, vol.35, No. 22, Oct. 1994, pp. 4874–4880.

* cited by examiner

Primary Examiner—P. Hampton-Hightower
(74) Attorney, Agent, or Firm—Schnader Harrison Segal & Lewis LLP

(57) ABSTRACT

Terminal-modified imide oligomers with an inherent viscosity of 0.05–1 obtained by reacting 2,3,3',4'-biphenyltetracarboxylic dianhydride, an aromatic diamine compound and 4-(2-phenylethynyl)phthalic anhydride, and their cured products. There are provided highly practical terminal-modified imide oligomers and their cured products, which cured products have satisfactory heat resistance and mechanical properties.

7 Claims, No Drawings

TERMINAL-MODIFIED IMIDE OLIGOMERS AND CURED PRODUCTS THEREOF

BACKGROUND OF THE INVENTION

1. Field of the Invention

The present invention relates to terminal-modified imide oligomers obtained by reacting a 2,3,3',4'-biphenyltetracarboxylic acid compound, an aromatic diamine compound and 4-(2-phenylethynyl)phthalic anhydride, and to their cured products.

Composite materials obtained as cured products by heat curing fiber-reinforced prepregs whose matrix resins are terminal-modified imide oligomers according to the present invention have excellent heat resistance and mechanical properties, and are particularly suitable for use in devices for the aeronautical and space industries.

2. Description of the Related Art

Cured products of terminal-modified imide oligomers exhibit excellent heat resistance and have long been known as matrix resins for molded products and fiber-reinforced composite materials.

As examples of such terminal-modified imide oligomers, Japanese Unexamined Patent Publication No. 64-54029 describes terminal-modified imide oligomers obtained by reacting a 2,3,3',4'-biphenyltetracarboxylic acid compound, an aromatic diamine compound and an unsaturated dicarboxylic acid such as nadic anhydride or an unsaturated monoamine compound such as propargylamine; Japanese Unexamined Patent Publication No. 64-54030 describes terminal-modified imide oligomers obtained by reacting a 3,3',4,4'-biphenyltetracarboxylic acid compound, an aromatic diamine compound and an unsaturated dicarboxylic acid such as nadic anhydride or an unsaturated monoamine compound such as propargylamine; and Japanese Unexamined Patent Publication No. 3-292130 describes a process for producing molded products of terminal-modified imide oligomers obtained by reacting a biphenyltetracarboxylic acid compound, an aromatic diamine compound and an unsaturated dicarboxylic acid such as maleic anhydride or an unsaturated monoamine compound such as propargylamine.

These terminal-modified imide oligomers modified with unsaturated monoamine compounds and terminal-modified imide oligomers modified with nadic anhydride all have low heat resistance as cured products.

There have recently been proposed, therefore, terminal-modified imide oligomers modified with 4-(phenylethynyl)phthalic anhydride.

For example, terminal-modified imide oligomers which are oligomers of 1,4-diaminobenzene and 2,2'-bis(3,4-dicarboxyphenyl)hexafluoropropane dianhydride and are terminal-modified with 4-(phenylethynyl)phthalic anhydride are described in "Polymer", 35, 4865 (1994), and terminal-modified imide oligomers obtained by reacting 3,3',4,4'-biphenyltetracarboxylic dianhydride, 1,1,1,3,3,3-hexafluoro-2,2-bis(3,4-dicarboxyphenyl)propane dianhydride, p-phenylenediamine and 4-(phenylethynyl)phthalic anhydride are described in "Polymer", 35, 4874 (1994).

However, these publicly known terminal-modified imide oligomers make use of special compounds as the essential aromatic tetracarboxylic dianhydrides.

BRIEF SUMMARY OF THE INVENTION

It is an object of the invention to provide novel, highly practical terminal-modified imide oligomers that give cured products with satisfactory heat resistance and mechanical properties (for example, elastic modulus, tensile strength and elongation), and also cured products thereof.

Specifically, the present invention relates to terminal-modified imide oligomers obtained by reacting a 2,3,3',4'-biphenyltetracarboxylic acid compound, an aromatic diamine compound and 4-(2-phenylethynyl)phthalic anhydride, and which are represented by the following formula:

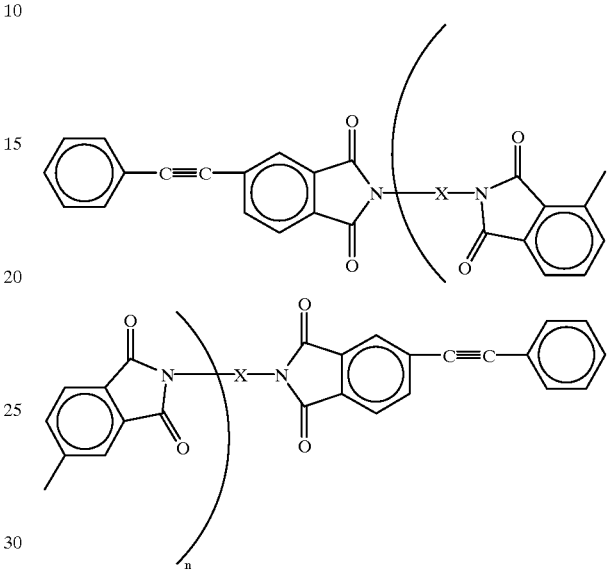

where X is an aromatic diamine residue and n is an integer, with an inherent viscosity ($\eta$inh, 30° C., 0.5 g/100 ml solvent, solvent: N-methyl-2-pyrrolidone) of 0.05–1, as well as to cured products comprising the terminal-modified imide oligomers alone or as composite materials with fibrous reinforcing materials.

DETAILED DESCRIPTION OF THE INVENTION

The terminal-modified imide oligomers of the invention are imide oligomers obtained by reacting a 2,3,3',4'-biphenyltetracarboxylic acid compound, an aromatic diamine compound and 4-(2-phenylethynyl)phthalic anhydride (hereunder abbreviated simply to "PEPA"), preferably in a solvent, where the equivalents for the total of each of the acid groups and equivalents for each amino group are approximately equal; the terminal-modified imide oligomers have an acetylenic addition-polymerizable unsaturated terminal group based on 4-(2-phenylethynyl)phthalic anhydride at either end (preferably both ends) of the imide oligomer and an imide bond on the imide oligomer main chain, the inherent viscosity is 0.05–1, preferably 0.05–0.5 and especially about 0.05–0.3, and they are relatively low molecular weight solids (powders) at normal temperature.

Terminal-modified imide oligomers with a melt viscosity in the range of 10 to 1 million poise, as the minimum melt viscosity before curing, are preferred. Also, terminal-modified imide oligomers with a post-curing glass transition point (Tg) of 300° C. or higher and a post-curing flexural strength of 1300 kgf/cm$^2$ or greater are preferred.

The minimum melt viscosity mentioned above is the temperature-dependent minimum value of the melt viscosity of the terminal-modified imide oligomer, which undergoes viscosity decrease with increasing temperature and viscosity increase due to the curing reaction.

The 2,3,3',4'-biphenyltetracarboxylic acid compound is 2,3,3',4'-biphenyltetracarboxylic acid, 2,3,3',4'-biphenyltetracarboxylic dianhydride (a-BPDA), or a lower alcohol ester, a salt or another derivative of 2,3,3',4'-biphenyltetracarboxylic acid, with 2,3,3',4'-biphenyltetracarboxylic dianhydride being ideal.

According to the invention, a portion of the 2,3,3',4'-biphenyltetracarboxylic acid compound (preferably 50 mole percent or less, more preferably 30 mole percent or less, and even more preferably 25 mole percent or less) may be replaced with another aromatic tetracarboxylic acid compound, for example 3,3',4,4'-biphenyltetracarboxylic dianhydride (s-BPDA), 3,3',4,4'-benzophenonetetracarboxylic dianhydride (BTDA), pyromellitic dianhydride, 2,2-bis(3,4-dicarboxyphenyl)methane or bis(3,4-dicarboxyphenyl) ether dianhydride.

As aromatic diamine compounds there may be mentioned 1,4-diaminobenzene, 1,3-diaminobenzene, 1,2-diaminobenzene, 2,6-diethyl-1,3-diaminobenzene, 4,6-diethyl-2-methyl-1,3-diaminobenzene, 3,5-diethyltoluene-2,4-diamine, 3,5-diethyltoluene-2,6-diamine, 4,4'-diaminodiphenyl ether (4,4-ODA), 3,4'-diaminodiphenyl ether (3,4-ODA), 3,3'-diaminodiphenyl ether, 3,3'-diaminobenzophenone, 4,4'-diaminobenzophenone, 3,3'-diaminodiphenylmethane, 4,4'-diaminodiphenylmethane, bis(2,6-diethyl-4-aminophenyl)methane, 4,4'-methylene-bis(2,6-diethylaniline), bis(2-ethyl-6-methyl-4-aminophenyl)methane, 4,4'-methylene-bis(2-ethyl-6-methylaniline), 2,2-bis(3-aminophenyl)propane, 2,2-bis(4-aminophenyl)propane, 1,3-bis(4-aminophenoxy)benzene (TPE-R), 1,3-bis(3-aminophenoxy)benzene, 1,4-bis(4-aminophenoxy)benzene, 1,4-bis(3-aminophenoxy)benzene, benzidine, 3,3'-dimethylbenzidine, 2,2-bis(4-aminophenoxy)propane, 2,2-bis(3-aminophenoxy)propane and 2,2-bis[4'-(4"-aminophenoxy)phenyl]hexafluoropropane, any of which may be used alone or in combinations of two or more.

Particularly preferred aromatic diamine compounds are 4,4'-diaminodiphenyl ether (4,4-ODA), 3,4'-diaminodiphenyl ether (3,4-ODA) and 1,3-bis(4-aminophenoxy)benzene (TPE-R).

According to the invention, 4-(2-phenylethynyl)phthalic anhydride is used as the unsaturated acid dianhydride for terminal modification (end capping).

The 4-(2-phenylethynyl)phthalic anhydride is preferably used at a proportion in the range of 5–200 mole percent, and especially 5–150 mole percent, with respect to the total acid.

As the solvent there may be mentioned N-methyl-2-pyrrolidone (NMP), N,N-dimethylformamide, N,N-dimethylacetamide (DMAc), N,N-diethylacetamide, N-methylcaprolactam, diethylene glycol dimethyl ether, triethylene glycol dimethyl ether, dioxane, tetrahydrofuran and γ-butyrolactone. These solvents may be used alone, or they may be used in combinations of two or more. The solvent may be selected based on publicly known techniques for soluble polyimides.

A terminal-modified imide oligomer according to the invention may be obtained, for example, by a method of using the 2,3,3',4'-biphenyltetracarboxylic acid compound (especially the acid dianhydride), an aromatic diamine compound and 4-(2-phenylethynyl)phthalic anhydride in amounts such that the total of equivalents of the acid groups of all the components is roughly equal to the total of the amino groups, polymerizing the components in the aforementioned solvent at a reaction temperature of about 100° C. or below, and especially 80° C. or below to produce an "oligomer with an amide-acid bond", and then adding an imidating agent to the amide-acid oligomer (also known as amic acid oligomer) at a low temperature of about 0–140° C., or by a method of heating at a high temperature of 140–275° C., for dehydrogenation and cyclization to obtain an imide oligomer with 4-(2-phenyethynyl)phthalic anhydride residues at the ends.

As a particularly preferred method for producing a terminal-modified imide oligomer of the invention there may be mentioned, for example, a method whereby the 2,3,3',4'-biphenyltetracarboxylic dianhydride, aromatic diamine and 4-(2-phenylethynyl)phthalic anhydride are first uniformly dissolved in the solvent and reacted at a reaction temperature of about 5–60° C. for about 1–180 minutes while stirring to produce an amic acid oligomer, and then the reaction solution is heated to a temperature of 140–275° C. and stirred at that temperature for 5–240 minutes for imidation reaction of the amic acid oligomer to produce an imide oligomer, subsequently cooling the reaction solution to near room temperature if necessary. In this reaction, it is preferred for all or some of the reaction steps to be carried out either in an inert gas atmosphere of nitrogen gas, argon gas or the like, or in a vacuum.

The terminal-modified imide oligomer produced in this manner may be used as a solution composition of the terminal-modified imide oligomer, if necessary, by pouring the reaction solution into water, etc., isolating it as a powder product and dissolving the powder product in a solvent if necessary for use, or alternatively the reaction solution may be used directly or as an appropriate concentrate or dilution.

The terminal-modified imide oligomer of the invention may consist of a mixture of oligomers with different molecular weights.

The terminal-modified imide oligomer of the invention may also be combined with other soluble polyimides.

The cured product of the terminal-modified imide oligomer of the invention is obtained by heat-curing the terminal-modified imide oligomer alone or as a composite material with a fibrous reinforcing material, in the presence or absence of a curing catalyst, by any known process, for example, injection molding. For injection molding, it is preferable to control the molecular weight of the terminal-modified imide oligomer to a number average molecular weight (Mn) of about 5000 and a melt viscosity of about 1000 poise at about 300° C., or to blend a high molecular weight oligomer of, for example, an Mn of about 20000 and a low molecular weight oligomer of, for example, an Mn of about 2000 to provide a blend of the terminal-modified imide oligomers of an Mn of about 5000 and a melt viscosity of about 1000 poise at about 300° C.

A solution composition of the terminal-modified imide oligomer may be coated onto a support and cured by heating at 260–500° C. for 5–200 minutes to make a film.

More preferably, a solution of a terminal-modified amic acid oligomer or a solution of a blend of a half-ester of an imide prepolymer and PEPA may be impregnated into a fibrous reinforcing material such as carbon fibers, dried by heating at 140–275° C. for about 5–240 minutes for imidation, and then the composite material may be heated at a temperature of 260–500° C. under normal pressure, preferably a pressure of 1–1000 kg/cm$^2$, for about one second to 100 minutes to produce a cured composite material.

Even more preferably, a terminal-modified imide oligomer solution may be impregnated into a fibrous reinforcing material such as carbon fibers, dried by heating at 100–275° C. for about 5–240 minutes, and then the composite material may be heated at a temperature of 260–500° C. under normal pressure, preferably a pressure of 1–1000 kg/cm², for about one second to 100 minutes to produce a cured composite material.

Alternatively, a powder of the terminal-modified imide oligomer may be packed into a die and compression molded at 10–260° C., 1–1000 kg/cm² for about one second to 100 minutes to form a preform, and then the preform may be heated at 260–500° C. for about 10 minutes to 40 hours under normal pressure with no pressure applied, for heat curing, to produce a cured product.

The terminal-modified imide oligomer is also usable for high temperature type adhesives, or selfstanding-bonding sheet in which two types of terminal-modified imide oligomer: one having a high molecular weight and the other having a low molecular weight.

The present invention will now be explained in further detail by way of examples and comparative examples.

The temperature for the minimum melt viscosity of the terminal-modified imide oligomer prior to curing and the melt viscosity at that temperature were measured using an RDSII Dynamic Spectrometer (measuring conditions: parallel plates, frequency: 1 Hz, temperature sweep measurement).

The mechanical properties of the film were determined according to ASTM D882, and the mechanical properties of the board were determined according to ASTM D790.

EXAMPLE 1

An amic acid oligomer was produced by a common method from 14.71 g (0.05 mole) of a-BPDA, 5.506 g (0.0275 mole) of 4,4-ODA, 5.506 g (0.0275 mole) of 3,4-ODA and 2.482 g (0.01 mole) of PEPA in 65.8 g of DMAc. The solution was cast coated onto a glass plate using an applicator and subjected to heat imidation (maximum temperature: 250° C.×30 minutes, vacuum) to obtain a terminal-modified imide oligomer. The oligomer had a theoretical Mn of 5240, a ηinh of 0.19, a Tg (DSC: differential scanning calorimetry) of 237° C. and a curing exothermal peak of 426° C. (initial heat: 360° C.). The uncured product was a brittle resin that was soluble in DMAc.

The minimum melt viscosity of the terminal-modified imide oligomer prior to curing was 860,000 poise (328° C.).

An NMP solution of the terminal-modified imide oligomer was coated onto a glass plate and heated to dryness, and then cured by heating (370° C.×2 hours) and released from the glass plate to obtain a film.

The cured product (film) had a Tg (DSC) of 310° C., and no exothermic peak was found. It was insoluble in DMAc and had an elastic modulus of 280 kg/mm², a tensile strength of 10.5 kg/mm², an elongation of 20% and a 5% weight reduction temperature of about 520° C. according to TGA (thermogravimetric analysis).

The terminal-modified imide oligomer was cured at 380° C. for 2 hours to form a cured board of 3 mm thick. The bending strength of the board was 1450 kgf/cm².

Comparative Example 1

A polyamic acid was produced by a common method from 14.71 g (0.05 mole) of a-BPDA, 5.505 g (0.0275 mole) of 4,4-ODA and 5.505 g (0.0275 mole) of 3,4-ODA in 100 g of DMAc. The solution was cast coated onto a glass plate using an applicator and a 40 μm polyimide film was obtained by a common method (maximum heat treatment conditions: 350° C.×30 minutes). The film had a Tg (DSC) of 285° C., an elastic modulus of 270 kg/mm², a tensile strength of 10 kg/mm², and an elongation of 30%.

EXAMPLE 2

A terminal-modified imide oligomer was produced in the same manner as Example 1 from 8.826 g (0.03 mole) of a-BPDA, 5 g (0.025 mole) of 4,4-ODA, 5 g (0.025 mole) of 3,4-ODA and 9.928 g (0.04 mole) of PEPA in 67 g of DMAc. The oligomer had a theoretical Mn of 1350, a ηinh of 0.08, a Tg (DSC) of 161° C. and a curing exothermal peak of 385° C. (initial heat: 360° C.). The uncured product was a brittle resin that was soluble in DMAc.

The minimum melt viscosity of the terminal-modified imide oligomer prior to curing was 470 poise (300° C.).

An NMP solution of the terminal-modified imide oligomer was coated onto a glass plate and heated to dryness, and then cured by heating (370° C.×2 hours) to obtain a film.

The cured product had a Tg (DSC) of 341° C., and no exothermic peak was found. It was insoluble in DMAc and had an elastic modulus of 300 kg/mm², a tensile strength of 11 kg/mm², an elongation of 7.5% and a 5% weight reduction temperature of about 520° C. according to TGA.

The terminal-modified imide oligomer was cured under the same conditions as in Example 1 to form a cured board of 3 mm thick. The board had a bending strength of 1450 kgf/cm².

EXAMPLE 3

A terminal-modified imide oligomer was obtained from 11.77 g (0.04 mole) of a-BPDA, 10.01 g (0.05 mole) of 4,4-ODA and 4.964 g (0.02 mole) of PEPA in 62 g of NMP, by heat imidation with heating at 180° C. for 4 hours. The oligomer had a theoretical Mn of 2490, a ηinh of 0.10, a Tg (DSC) of 200° C. and a curing exothermal peak of 357° C. The uncured product was a brittle resin that was soluble in DMAc.

The minimum melt viscosity of the terminal-modified imide oligomer prior to curing was 14,000 poise (316° C.).

The terminal-modified imide oligomer was cured by heating (380° C.×2 hours) to fabricate a cured product (test piece) with a thickness of 3 mm, and a flexural test according to ASTM D-790 resulted in a flexural strength of 1490 kgf/cm². The cured product had a Tg (DSC) of 375° C., and no exothermic peak was found. It was insoluble in DMAc and had an elastic modulus of 290 kg/mm², a tensile strength of 11.5 kg/mm², an elongation of 20% and a 5% weight reduction temperature of about 520° C. according to TGA.

EXAMPLE 4

A terminal-modified imide oligomer was obtained from 23.54 g (0.08 mole) of a-BPDA, 26.30 g (0.09 mole) of TPE-R and 4.964 g (0.02 mole) of PEPA in 140 g of NMP, by heat imidation with heating at 180° C. for 4 hours, followed by reprecipitation in water. The oligomer had a theoretical Mn of 5160, a ηinh of 0.18, a Tg (DSC) of 225° C. and a curing exothermal peak of 357° C., and it was a brittle resin that was soluble in DMAc.

The minimum melt viscosity of the terminal-modified imide oligomer prior to curing was 29,000 poise (310° C.).

The terminal-modified imide oligomer was cured by heating (370° C.×2 hours) to fabricate a cured product (test piece) with a thickness of 3 mm, and a flexural test according to ASTM D-790 resulted in a flexural strength of 1600 kgf/cm². The cured product had a Tg (DSC) of 310° C., and no exothermic peak was found. It was insoluble in DMAc and had an elastic modulus of 270 kg/mm², a tensile strength of 10 kg/mm², an elongation of 35% and a 5% weight reduction temperature of about 520° C. according to TGA.

EXAMPLE 5

A terminal-modified amic acid oligomer solution (DMAc solution, 35% solid content) was obtained under the same conditions as Example 1. This was used as an impregnating solution to impregnate carbon fibers (Besfight HTS3000, product of Toho Rayon) under conditions of 50% humidity and 25° C. temperature, which were coiled up with a drum winder and aligned parallel in the same direction, subsequently dried at 100° C. for 30 minutes and then under a nitrogen stream at 270° C. for 30 minutes, and imidated to make a composite material.

The composite material (thickness: 150 μm) was cut into 150 mm squares, and 8 squares were stacked in the same direction and pressed under conditions of 380° C., 20 kg/cm$^2$ for 30 minutes, and then cooled to 100° C. while holding the pressure to obtain a cured composite material. A prescribed test piece was cut out of the flat sheet to measure the internal void percentage and the flexural strength and flexural modulus, according to ASTM D-790. The internal void percentage was determined from the sheet density and the fiber-containing weight percentage. The results were as follows.

Flexural modulus: 14,200 kg/mm$^2$

Flexural strength: 227 kg/mm$^2$

Bulk fiber content: 61%

Bulk cavity content: 0.3%

EXAMPLE 6

A cured composite material was obtained in the same manner as Example 5, except that the terminal-modified oligomer obtained in Example 4 was dissolved in NMP (35% by weight) to make an impregnating solution. The results were as follows.

Flexural modulus: 13,500 kg/mm$^2$

Flexural strength: 220 kg/mm$^2$

Bulk fiber content: 60%

Bulk cavity content: 0.2%

According to the present invention it is possible to obtain novel, highly practical terminal-modified imide oligomers.

The present invention also makes it possible to obtain cured products of these novel terminal-modified imide oligomers, that exhibit satisfactory heat resistance and mechanical properties such as elastic modulus, tensile strength and elongation.

What is claimed is:

1. An end-capped imide oligomer obtained by reacting a 2,3,3',4'-biphenyltetracarboxylic acid compound, an aromatic diamine compound and 4-(2-phenylethynyl)phthalic anhydride and represented by the following formula:

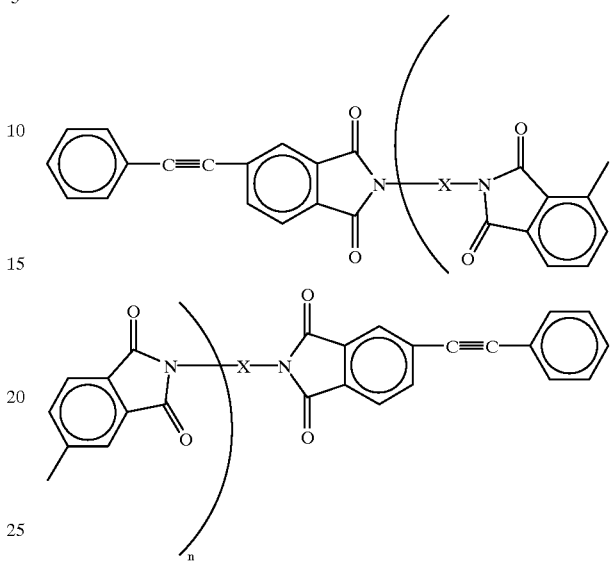

where X is an aromatic diamine residue and n is an integer, with an inherent viscosity (ηinh, 30° C., 0.5 g/100 ml solvent, solvent: N-methyl-2-pyrrolidone) of 0.05–1.

2. An end-capped imide oligomer according to claim 1, which has an inherent viscosity of 0.05–0.5.

3. An end-capped imide oligomer according to claim 1, wherein the minimum melt viscosity prior to curing is in the range of 10 to 1 million poise.

4. An end-capped imide oligomer according to claim 1, wherein the glass transition point (Tg) after curing is 300° C. or above.

5. An end-capped imide oligomer according to claim 1, wherein the flexural strength after curing is 1300 kgf/cm$^2$ or greater.

6. A cured product obtained by heat-curing of an end-capped imide oligomer according to claim 1 or 2 alone.

7. A cured product obtained by heat-curing of a composite material which comprises an end-capped imide oligomer according to claim 1 or 2 and fibrous reinforcing material.

* * * * *